US00PP18245P2

(12) United States Plant Patent
Van Zanten

(10) Patent No.: US PP18,245 P2
(45) Date of Patent: Nov. 20, 2007

(54) ***OSTEOSPERMUM* PLANT NAMED 'GG DEL PC06'**

(50) Latin Name: *Osteospermum ecklonis*
Varietal Denomination: GG DEL PC06

(75) Inventor: Leo Van Zanten, Oxnard, CA (US)

(73) Assignee: G & G Breeding Corporation, Oxnard, CA (US)

( * ) Notice: Subject to any disclaimer, the term of this patent is extended or adjusted under 35 U.S.C. 154(b) by 0 days.

(21) Appl. No.: 11/396,068

(22) Filed: Mar. 31, 2006

(51) Int. Cl.
*A01H 5/00* (2006.01)

(52) U.S. Cl. ..... Plt./360
(58) Field of Classification Search ..... Plt./360
See application file for complete search history.

*Primary Examiner*—Wendy C. Haas
*Assistant Examiner*—Georgia Helmer

(57) ABSTRACT

A new and distinct *Osteospermum* plant cultivar is disclosed, characterized by large daisy type inflorescences, freely flowering under outdoor growing conditions with continuous blooming from spring through autumn, pale purple ray florets with a dark violet base, and dark blue disc florets.

1 Drawing Sheet

Latin name of the genus and species: *Osteospermum ecklonis.*
Variety denomination: 'GG DEL PC06'.

BACKGROUND OF THE INVENTION

The new cultivar 'GG DEL PC06' is a product of open pollination in a heterogeneous population of *Osteospermum* mass selection. The new cultivar was discovered and selected by Leo Van Zanten in May 2004 in Carpinteria, Calif.

Asexual reproduction of the new cultivar 'GG DEL PC06' by cuttings from adventitious shoots were performed in Oxnard, Calif., and has shown that the unique features of this new cultivar are stable and reproduced true to type on successive generations.

SUMMARY OF THE INVENTION

The cultivar 'GG DEL PC06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG DEL PC06.' These characteristics in combination distinguish 'GG DEL PC06' as a new and distinct *Osteospermum* cultivar.

1. Large daisy type inflorescence;
2. Pale purple ray florets;
3. Dark blue disc florets; and
4. A free branching habit.

There is no parent variety to compare to 'GG DEL PC06.'

In comparison to the commercially available variety 'Duesumpink' (U.S. Plant Pat. No. 15,938) 'GG DEL PC06' is taller and wider. Also, 'GG DEL PC06' has a wider inflorescence diameter and depth. Further, 'GG DEL PC06' has a wider disc diameter. Finally, the ray florets of the comparable variety 'Duesumpink' fade to a lighter color toward the base of the florets while the new variety's ray florets intensify in color toward the base.

BRIEF DESCRIPTION OF THE PHOTOGRAPH

The accompanying photograph drawing illustrates in full color a typical plant of 'GG DEL PC06' grown in a 6-inch pot, planted late October and grown outdoors. The plant is 18 weeks old. The growing temperature ranged from 12° C. to 15° C. at night to 12° C. to 20° C. during the day. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG DEL PC06' plants grown in Oxnard, Ventura County, Calif., during the months of October through February. The growing temperature ranged from 12° C. to 15° C. at night to 12° C. to 20° C. during the day. Measurements and numerical values represent averages of typical flowering types.

Botanical classification: *Osteospermum ecklonis* cultivar 'GG DEL PC06.'
Commercial classification: Garden-type *Osteospermum.*

PROPAGATION

Time to rooting: 10 to 14 days at approximately 21° C.
Root description: Fine, fibrous.

PLANT

Growth habit: Mounding outwardly spreading herbaceous perennial.
Height: Approximately 25 cm.
Plant spread: Approximately 39 cm.
Growth Rate: Vigorous.
Branching characteristics: Free Branching.
Length of lateral branches: Approximately 9 cm.
Number of leaves per lateral branch: Approximately 59.
Age of plant described: Approximately 127 days.

FOLIAGE

Leaf:
*Arrangement.*—Alternate single.
*Average length.*—Approximately 3.9 cm.
*Average width.*—Approximately 1.7 cm.
*Shape of blade.*—Obovate.
*Apex.*—Abruptly acuminate.
*Base.*—Attenuate.
*Attachment.*—Stalked.
*Margin.*—Entire with occasional tiny serrations.
*Texture of top surface.*—Lightly pubescent.
*Texture of bottom surface.*—Lightly pubescent.
*Leaf internode length.*—Approximately 2 cm.
*Color.*—Young foliage upper side: Near Green 137A. Young foliage under side: Near Green 137B. Mature foliage upper side: Near Yellow-Green 147A. Mature foliage under side: Near Green 137A.
*Venation.*—Type: Pinnate. Venation color upper side: Near Green 143D. Venation color under side: Near Green 143D.

Petiole:
*Average length.*—Approximately 1.5 cm.
*Color.*—Near Green 143D.
*Diameter.*—Approximately 0.2 cm.

BLOOM

Inflorescence:
*Flowering habit.*—Freely flowering under outdoor growing conditions with continuous blooming from spring through autumn and year round in a greenhouse environment.
*Inflorescence form.*—Daisy.
*Natural flowering season.*—Continuous throughout February to September in temperature regions.
*Number of inflorescences per lateral branch.*—Approximately 4.
*Inflorescence diameter.*—Approximately 5.5 cm.
*Inflorescence depth.*—Approximately 3.4 cm.
*Disc diameter.*—Approximately 1.4 cm.
*Inflorescence longevity on plant.*—Approximately 5 to 10 days; longevity of individual flowers are very dependent on temperature and light conditions.
*Persistence.*—Persistent.

Ray florets:
*Appearance.*—Matte.
*Texture.*—Smooth.
*Average number of ray florets per inflorescence.*—21.
*Shape.*—Oblanceolate.
*Aspect.*—Slightly cupped, facing upward or outward.
*Margin.*—Entire.
*Apex.*—Abruptly acuminate.
*Length.*—Approximately 3.5 cm.
*Width.*—Approximately 0.5 cm.
*Color.*—Upper surface at first opening: Near Red-Purple 69D with faint longitudinal stripes of near Red-Purple 69A. The very tip is near Purple 79A and the base is near Violet-Blue 93A. Upper surface at maturity: Near Red-Purple 69A with faint longitudinal stripes of Red-Purple 70D. The very tip is near Purple 79A and the base is near Violet-Blue 93A. Upper surface at fading: Near Red-Purple 69A with faint longitudinal stripes of Red-Purple 70D. The very tip is near Purple 79A and the base is near Violet-Blue 93A. Under surface at first opening: Near Violet 85C with longitudinal stripes of near Purple 79A to the very tip. Under surface at maturity: near Violet 85B with longitudinal stripes of near Purple 79A to the very tip. Under surface at fading: Near Violet 84B with longitudinal stripes of near Purple 79A to the very tip.

Disc florets:
*Appearance.*—Shiny.
*Texture.*—Smooth.
*Average number of florets per disc.*—Approximately 77.
*Shape.*—Tubular.
*Apex.*—Five-pointed.
*Average length.*—Approximately 0.5 cm.
*Average width.*—Approximately 0.1 cm.
*Color.*—At first opening: Near Blue 103B at very center with near Violet-Blue 93C at edge of disc. At maturity: Near Blue 103B. At fading: Near Blue 103B.

Peduncle:
*Length.*—Approximately 8 cm.
*Angle.*—Terminal peduncles, erect; secondary and tertiary peduncles, about 45° from vertical.
*Strength.*—Moderate.
*Color.*—Near Yellow-Green 144A with shades of Yellow-Green 147A.
*Habit.*—Upright.
*Diameter.*—Approximately 0.1 cm.
*Surface texture.*—Lightly pubescent.

Inflorescence Bud:
*Length.*—Approximately 2.5 cm.
*Diameter.*—Approximately 0.5 cm.
*Form.*—Elliptic.
*Color.*—Near Purple 79B.

Involucral bracts (Phyllaries):
*Appearance.*—Matte.
*Texture.*—Lightly pubescent.
*Number.*—Approximately 20.
*Shape.*—Lanceolate.
*Margin.*—Entire.
*Apex.*—Narrowly acute.
*Length.*—Approximately 1.8 cm.
*Width.*—Approximately 0.2 cm.
*Color.*—Upper side: Near Green 137B. Under side: Near Green 138B.

REPRODUCTIVE ORGANS

*Androecium.*—Present on disc florets only. Number of stamens: 5. Anther shape: Linear. Anther length: Approximately 1.4 mm. Anther color: Near Blue 103B. Amount of pollen: Not abundant. Pollen color: Near Yellow-Orange 21A.
*Gynoecium.*—Present on ray and disc florets. Pistil Number: One. Pistil length: Approximately 6 mm. Stigma shape: Two parted. Stigma length: Approximately 1.2 mm. Stigma color: Near Purple 79A. Style length: Approximately 0.1 cm. Style color: Near Purple 79A.

OTHER CHARACTERISTICS

Disease resistance: Neither resistance nor susceptibility to diseases or pests has been observed in this variety.
Drought tolerance/cold tolerance: Plants are moderately drought tolerant. Plants need cold, less than 12.8° C. for flower induction.
Fruit/seed production: Commercially, this plant is not used or observed in a stage where seeds would be produced. Therefore, seed production has not been observed.

What is claimed is:

1. A new and distinct cultivar of *Osteospermum* plant named 'GG DEL PC06' as herein illustrated and described.

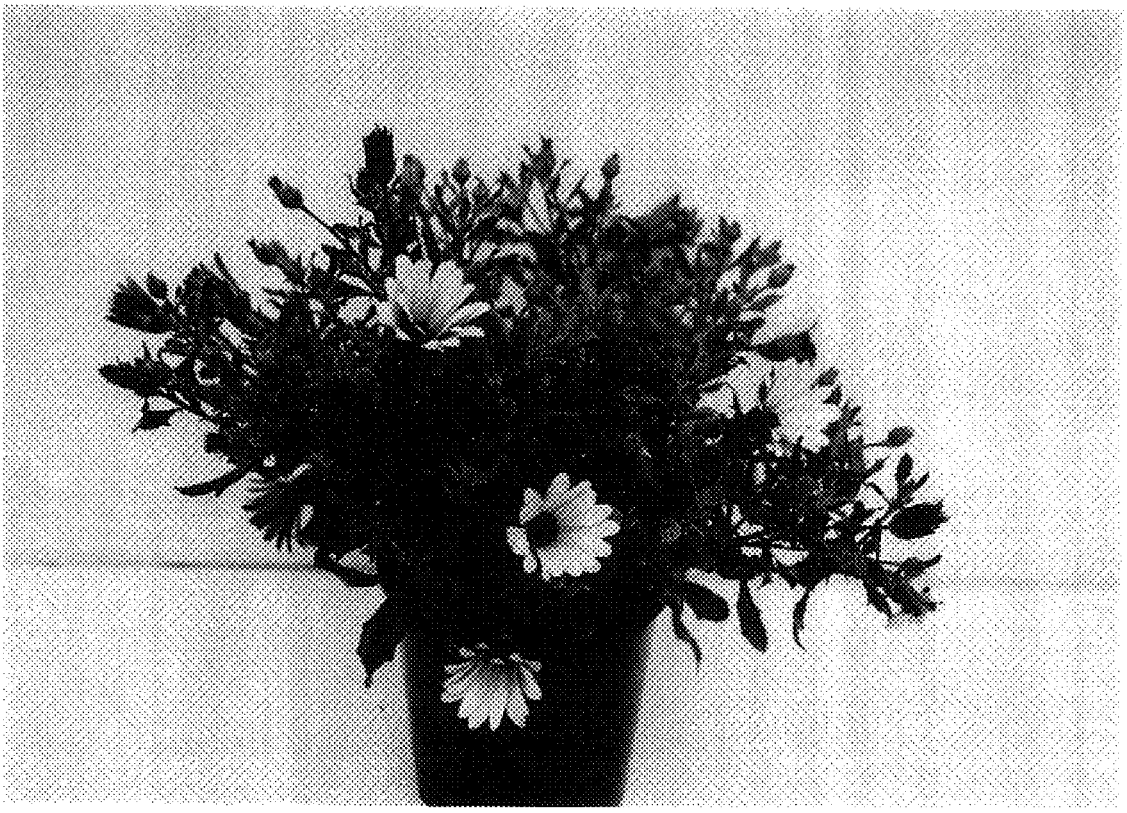

* * * * *